United States Patent [19]
Hanson

[11] Patent Number: 5,540,586
[45] Date of Patent: Jul. 30, 1996

[54] ELASTOMERIC ORTHODONTIC LIGATURES

[76] Inventor: G. Herbert Hanson, 57 Augusta Street, Hamilton, Ontario, Canada, L8N 1P8

[21] Appl. No.: 321,014

[22] Filed: Oct. 6, 1994

Related U.S. Application Data

[63] Continuation-in-part of Ser. No. 36,639, Mar. 24, 1993, Pat. No. 5,380,197.

[51] Int. Cl.$^6$ ........................................................ A61C 3/00
[52] U.S. Cl. ........................ 433/22; 433/11; 433/13
[58] Field of Search ................................ 433/10, 13, 14, 433/15, 18, 22, 11

[56] References Cited

U.S. PATENT DOCUMENTS

| | | | |
|---|---|---|---|
| 3,052,027 | 9/1962 | Wallshein | 433/22 X |
| 3,913,228 | 10/1975 | Wallshein | 433/18 |
| 4,900,250 | 2/1990 | Kesling | 433/18 X |
| 5,044,946 | 9/1991 | Cleary | 433/22 X |
| 5,356,288 | 10/1994 | Cohen | 433/13 X |

Primary Examiner—Nicholas D. Lucchesi
Attorney, Agent, or Firm—Rogers & Scott

[57] ABSTRACT

A reinforced elastomeric non-hoop ligature comprises a thin flat body of the elastomeric material having incorporated therein a thin flat rigid insert of gingival-occlusal dimension greater than the corresponding dimension of the arch-wire receiving slot of the orthodontic bracket with which it is employed. The ligature body has holes or slots through which ligature retaining projections of the bracket body protrude, and when mounted on the bracket the rigid member straddles the bracket slot mouth. A reinforced hoop ligature comprises a torus of the elastomeric material with two diametrically opposed rigid inserts of gingival-occlusal dimension sufficient to straddle the bracket slot. The rigid insert or inserts increase the cooperative action between the arch wire and the ligature to facilitate the bracket and tooth movement, and when the arch wire is fully within the slot provides the possibility of controlling sliding friction between the arch wire and the bracket, including minimising when this is desirable. The mesial distal widths of the body and insert and the labial-lingual position of the insert can be varied in to provide the characteristics required.

20 Claims, 4 Drawing Sheets

ELASTOMERIC ORTHODONTIC LIGATURES

This application is a continuation-in-part of prior application Ser. No. 08/036,639, filed Mar. 24, 1993, now U.S. Pat. No. 5,380,197.

FIELD OF THE INVENTION

This invention provides new orthodontic products comprising elastomeric orthodontic ligatures for use in combination with orthodontic brackets and arch wires.

REVIEW OF THE PRIOR ART

The majority of orthodontic procedures employ a set of brackets that are attached to respective teeth, originally by attaching them to metal bands which embrace the teeth, but now more usually by cementing them directly to the teeth. In the procedure now most commonly used the brackets are connected together by an arch wire, so called because it is preformed to an optimum arch shape corresponding to the desired final conformation of the teeth, the wire being engaged in mesially-distally extending slots in the brackets, which slots are usually of rectangular cross section. The wire is attached to the brackets for the desired cooperation between them by one of the usually available ligating means. Originally such means consisted of ligating wires twisted about the respective bracket and the arch wire, but with the development of suitable elastomeric materials they have increasingly been replaced by elastomeric hoops (sometimes also referred to colloquially as loops, rings or donuts) engaged over gingivally and occlusally protruding elements of the brackets, such hoops being easier and quicker to apply and avoiding the difficulty with wires that the trimmed twisted wire ends must be kept out of contact with soft tissue in the mouth.

Elastomeric hoops also have the advantage over ligating wires that their resilience enables them to cooperate with the bracket and arch wire in facilitating the procedure. Thus, the ligating wires have no spring and therefore their only function is to hold the bracket and wire together as tightly as possible and restrain them against movement away from one another; as they move toward one another the wire slackens and must be retightened periodically. The resilience of the ligating hoops enables them to be engaged with the bracket and wire while they are displaced, and they will remain in engagement without the need for such periodic adjustment. Moreover their resilience can be made to supplement the operational tooth-moving force provided by the springy arch wire.

Another form of ligating means that increasingly is replacing both the wires and elastomeric ligating hoops are springs or spring urged latches that are parts of the brackets. These have the advantage of the elastomeric hoops that they can provide an auxiliary spring force and, in the case of those employed for example in my prior art spring self adjusting brackets, as disclosed in my U.S. Pat. Nos. 3,772,787; 4,248,588; and U.S. Pat. No. 4,492,573, have the additional advantage that they engage with the arch wire over a considerably greater length and area and are therefore able to provide faster and more effective cooperation between the bracket and the wire.

In a typical procedure the first arch wire employed is an undersize multistrand very springy wire of circular transverse cross section, and of low load deflection rate, the wire being a loose fit in the bracket slots so that the correcting forces it can apply to the brackets, and thus to the teeth, are correspondingly small, as is desired to avoid the possibility of tissue damage and/or root resorption. After several weeks the corrective effect of this undersize wire decreases to an inefficient value, and it is then replaced with a less springy wire of larger diameter; this successive replacement of round wires is continued until the one in use is of the largest diameter that can be inserted in the slot while not producing excessive sliding friction between the wire and the brackets that would inhibit any desired mesial or distal movement of the brackets along the wire. This largest arch wire may still be of springy material, and can then be replaced by wires of progressively increasing stiffness. Alternatively, the diameter and the stiffness may be increased together. At some stage the round cross section wires are replaced, usually by rectangular cross section wires, which cooperate with the rectangular cross section slots to give greater control of tipping (commonly called "torquing") of the teeth about a mesial distal axis. During some stages of the procedure, usually the earlier stages, the brackets may be connected by tension springs to produce the desired retraction or protraction movements of the teeth.

It is a continuing desire to provide orthodontic devices and procedures that permit and facilitate the use of relatively light correcting forces during all stages of a procedure, especially since it is found that appropriate use of these light forces can result in corrective procedures that are at least as fast, and can even be significantly faster, than prior devices and procedures using heavier forces, while providing the above described reduced risk of damage to teeth and supporting tissues. For convenience in discussion the movement of any tooth during a procedure may be considered as potentially involving six resultant movements, any combination of which may be required for the tooth to reach its optimum position; in practice the movement involving from any one up to all six. Three are linear displacements mesially-distally, labially-lingually and gingivally-occlusally, while the other three are rotations about respective axes mutually at right angles to one another, namely a gingival occlusal axis (rotation), a mesial distal axis (tipping or torquing) and a lingual labial axis (angularion). During the stages predominantly involving first order displacements and rotations it is preferred to minimize mesial-distal sliding friction between the bracket and arch wire, so that the brackets can move easily along the wire under its gentle persistent urge, a substantially larger force being required if there is much such friction to overcome. During the stages predominantly involving rotations and second order displacements a certain amount of this sliding friction can be advantageous to prevent undesired regressive movement along the wire away from the established mesial distal positions.

The minimisation of mesial-distal sliding friction is difficult with brackets used with known wire and hoop elastomeric ligatures, since the ligatures usually must engage the arch wire quite tightly throughout the procedure in order to perform their intended function. It is much less difficult with brackets employing ligating metal springs, since during the initial stages while the wire protrudes from the slot the metal wire-to-metal spring coefficient of friction inherently is lower, until the wire is fully home in the slot the area of contact between the spring and the wire usually is much smaller, and the contact forces involved are smaller. Because of the recognised importance of being able to provide minimum friction when required, new brackets have been proposed for use with wire and elastomeric hoop ligatures in which the ligation hoop embracing the bracket body can only contact the wire if it protrudes from the slot, this condition obtaining until rotation and tipping of the tooth is completed and the wire is fully within the slot. Thereafter the wire cannot be heavily engaged by the ligature while the tooth is moved mesially or distally in this optimum attitude with accompanying movement of the bracket along the wire. An example of such a bracket is that disclosed in my U.S. Pat. No. 5,154,607, issued Oct. 13, 1992, the disclosure of which is incorporated herein by this reference. The adoption of these special brackets involves a substantial change in the technique employed by the orthodontist.

SUMMARY OF THE INVENTION

The invention provides new orthodontic products comprising elastomeric ligatures having reinforced or stiffened portions and engageable with the bracket and the arch wire in a manner such that sliding friction between the arch wire and the ligature can be adjusted.

The ligatures can be used with a wide range of existing brackets as well as with the above-described low friction brackets.

DESCRIPTION OF THE DRAWINGS

Particular preferred embodiments of the invention will now be described, by way of example, with reference to the accompanying diagrammatic drawings, wherein.

DESCRIPTION OF THE PREFERRED EMBODIMENTS

For convenience in description the embodiments are illustrated and described herein and claimed in the appended claims as they would be used in the conventional so-called labial technique, in which the brackets are attached to the labial surfaces of the teeth. The ligatures of the invention are equally usable in the so-called lingual technique, in which the brackets are attached to the lingual surfaces of the teeth so that they are concealed from view as much as possible. It is usual in orthodontic bracket manufacture to avoid very sharp edges between meeting surfaces, particularly with ceramic brackets, in order to avoid the production of stress concentration points and edges and the surfaces may merge so smoothly with one another that there is no definite junction between them. Similarly, and for the same purpose, sharp corners and sharp edges between meeting surfaces are avoided in the manufacture of the ligatures of the invention. The same number reference is used for similar parts wherever that is possible.

Figures 1, 2:
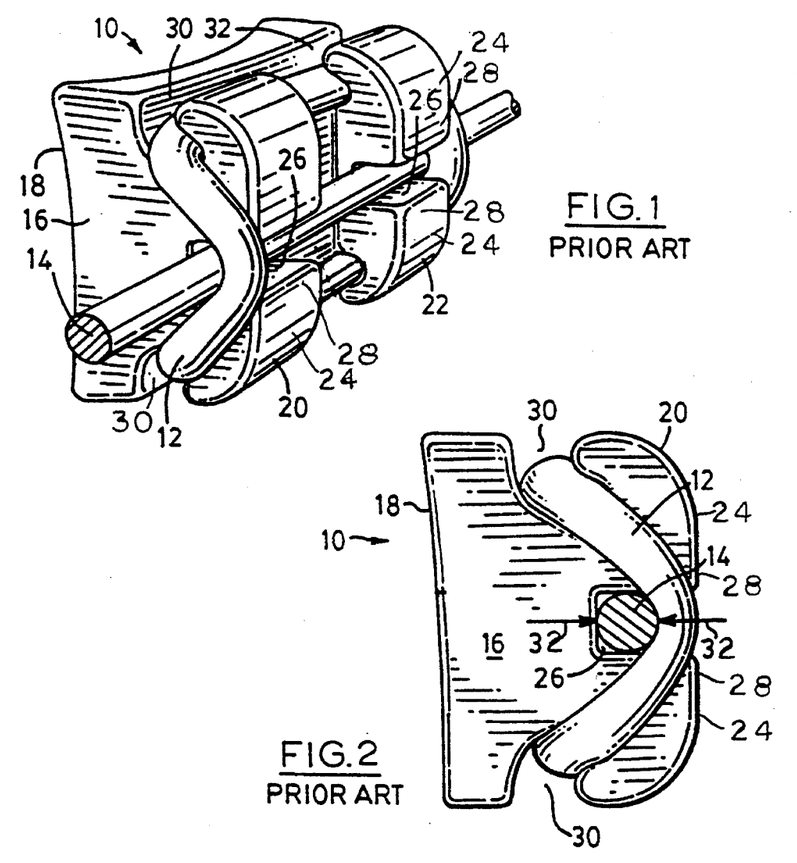
FIG. 1 is a perspective view of a conventional prior art double tie wing orthodontic bracket with an arch wire engaged in its slot, the arch wire being retained in the slot by a prior art elastomeric hoop ligature.
FIG. 2 is a side elevation from the mesial or distal of the bracket, arch wire and ligature combination of FIG. 1.

FIGS. 1 and 2 illustrate a typical prior art orthodontic bracket 10 as used in a labial system in conjunction with an elastomeric ligating hoop 12 (or with a tie wire which is not illustrated) to connect the bracket to an arch wire 14 on which it is mounted. The bracket body can be of stainless steel or ceramic material and consists of a body 16, the lingual face 18 of which is shaped to conform relatively closely to the labial tooth face to which it is applied. The body is provided with ligature retaining means comprising two mesially-distally spaced, occlusally-gingivally extending pairs of tie wings 20 and 22 having respective labial faces 24; to prevent undesired rotations these tie wings are spaced mesially-distally as far apart as possible. Each pair is provided with a respective arch wire slot 26 of rectangular cross-section and opening to the respective labial face 24, the border portions of the labial faces 24 bordering the slots 26 having the reference 28. The tie wings may extend gingivally and occlusally to about the same extent as the bracket body and are provided with ligature receiving slots 30, these slots being undercut labially a substantial distance into the tie wings to ensure that the ligature will not slip off the bracket body as it becomes flaccid in use. The arch wire 14 may be of circular cross section as illustrated, in which case the wire and bracket can rotate relative to one another about a mesial-distal extending axis, or it can be of rectangular or part rectangular cross-section (see FIGS. 9 through 12 and 14), in which case such rotation is prevented and the wire and bracket move together.

The prior art ligature 12 shown is of typical construction and consists of an elastomeric ring of circular transverse cross-section (i.e. a toroid). The ligature receiving slots 30 are disposed closer to the body lingual face than are the lingual faces of the slots 26 in order to permit the ligature to press an undersize or a round arch wire into contact with the slot lingual wall for control of tooth rotation about the occlusal-gingival axis. This known bracket and ligating hoop structure has the disadvantage that, except in stages of a procedure that the wire is completely out of contact with the slot lingual surface, there is pressure engagement of the wire with the lingual slot face under the urge of the ligature, whether or not friction is desired at this stage. Also, there is always constant engagement of the elastomeric ligature with the metal wire, and such elastomer to metal contact usually involves higher friction than metal to metal contact. The forces resulting from this pressure and provided by the ligature are indicated in FIG. 2 by the arrows 32. Consequently there is always considerable frictional resistance to sliding movement of the bracket along the wire, and this is counterproductive in the stages where free sliding movement is necessary for efficient tooth movement and alignment.

With the orthodontic technique in which this type of bracket is employed each bracket is attached to its respective tooth in an attitude such that, as each successive arch wire attempts to return to its preformed arch shape, the teeth are moved toward their desired optimized positions and attitudes, at which time the arch wire fits as snugly as possible within the slot without protruding therefrom, as illustrated by FIGS. 1 and 2, and the ligating means is in its least-strained position. To achieve this the torque requirements (rotation about a mesial distal axis), angularion requirements (rotation about a labial lingual axis), and first order pre-adjustments, are obtained by suitable shaping of the bracket bases, particularly of their lingual surfaces and variation of their thicknesses, so that all of the bracket labial faces 24 will be aligned when the teeth are in their optimum attitudes and rotational positions. In practice the first-used smaller sized arch wires will usually be unable to achieve this, and it is desired that most of it be achieved, and if possible all of it be achieved, before the last wire is used, so that the principal function of that last wire will be any final tipping and rotation of the teeth, together with any finally required anterior or posterior movement which, as described above, has previously usually been achieved by use of a rectangular cross section wire operating in a rectangular cross section slot. The slot lingual surface usually is curved to conform as closely as practicable to the optimized arch wire shape; such curvature usually is not needed with the brackets attached to the bicuspids and molars since the corresponding parts of the arch wire are almost straight.

Figure 5:
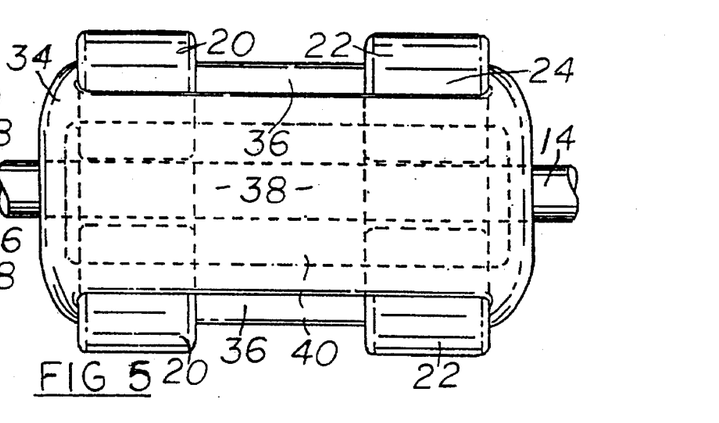
FIG. 5 is an elevation similar to FIG. 3 and showing the ligature mounted on the double tie wing bracket.
Figure 6:
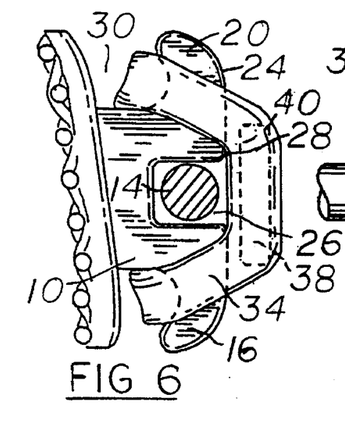
FIG. 6 is an elevation from the mesial or distal of the bracket, arch wire and ligature combination of FIG. 5.

FIGS. 3 through 6 show the structure of a reinforced or stiffened elastomeric ligature of the invention intended for use with a conventional prior art double tie wing bracket as illustrated by FIGS. 1 and 2. This first embodiment consists of a flat body 34 that is approximately rectangular as seen in labial or lingual elevation when relaxed and unmounted, and that is of a suitable elastomeric material, such as a rubber/polyurethane formulation of durometer stiffness or hardness from 70–75, preferably 75, as sold for example by Dow Chemical Inc. The body has formed therein two gingivally-occlusally spaced, mesially-distally extending elongated slots 36 through which the ligature retaining tie wings 20 and 22 protrude when it is in place on the bracket, as illustrated by FIGS. 5 and 6. The portion of the ligature body between the two slots 36 has incorporated therein a thin flat member 38 of gingival-occlusal dimension greater than the corresponding height dimension of the slot 26, so that it bridges or straddles the slot labial opening and has its gingival and occlusal border portions 40 pressing respectively through the intervening thin layer of elastomer against the slot border portions 28 of the bracket labial face. The member is of a material that is considerably more rigid than the elastomer of the ligature body and, with the arch wire fully inside the slot, as illustrated by FIG. 6, the rigid member provides a correspondingly firm barrier to the escape of the wire from the slot. The rigid member cannot enter the slot at all and at most only the very thin layer of elastomer on its lingual surface can protrude into it, so that the possibility of high frictional contact between the wire and the slot lingual surface, and between the wire and the ligature, is correspondingly controlled, and can be reduced to a minimum, as will be discussed in more detail below.

Figure 7:
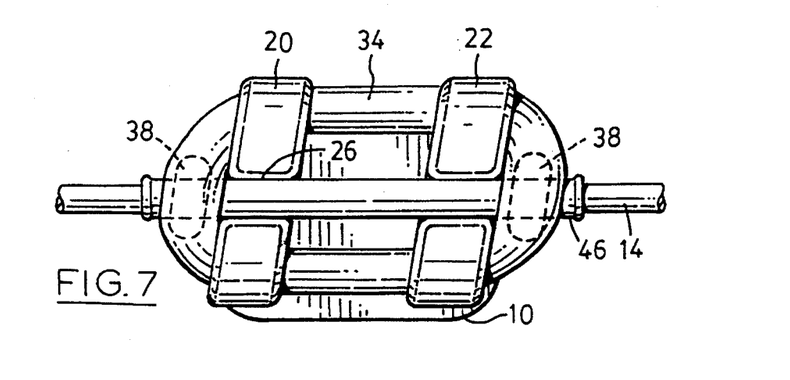
FIG. 7 is an elevation from the labial of a double tie wing bracket showing in place thereon a reinforced elastomeric hoop ligature that is another embodiment of the invention.

FIG. 7 (sheet 4) shows a reinforced hoop ligature of the invention also applied to a conventional double tie wing bracket of the type shown in FIGS. 1 and 2. The body of the ligature has the form of a torus which is looped around the ligature receiving members, and it is provided with two separate diametrically opposed rigid reinforcing members 38, each of which is of gingival occlusal dimension greater than that of the slot opening so that its border portions 40 will engage the slot border portions 28 for operation as with the non-hoop ligatures described above.

The material from which the inserts are made must of course be much more rigid than that of the ligature body and usually they will be metal or ceramic wafers. The wafer may be embedded centrally in the ligature so as to be completely surrounded symmetrically on all sides by elastomeric material, as shown in solid lines in FIG. 4 and in broken lines in FIGS. 6, 9 through 13, 15, 17 and 19, in which case as mentioned above there is still the possibility of limited protrusion of the thin lingual-side layer of elastomer into the slot. Alternatively, as shown in broken lines in FIG. 4 and solid lines in FIG. 19, it can be offset in the body toward the lingual so as to have its lingual face exposed and contacting the bracket body labial face 24, in which case there can be no protrusion at all of the ligature into the slot, reducing the possibility of friction to a minimum. In other embodiments that are not illustrated, although the insert is completely embedded it is still offset toward the lingual so that the lingual-side layer of elastomer is thinner than the labial-side layer, thus providing further control of the possibility of protrusion into the slot. Any suitable metal or ceramic will inherently be of sufficient stiffness, but the inserts can also be of a compatible plastics material of sufficient stiffness. Inserts of plastics material will usually need to be thicker than those of metal or ceramic, and similarly those of a ceramic material, such as alumina, will generally need to be of greater thickness than those of metal.

Figure 8:
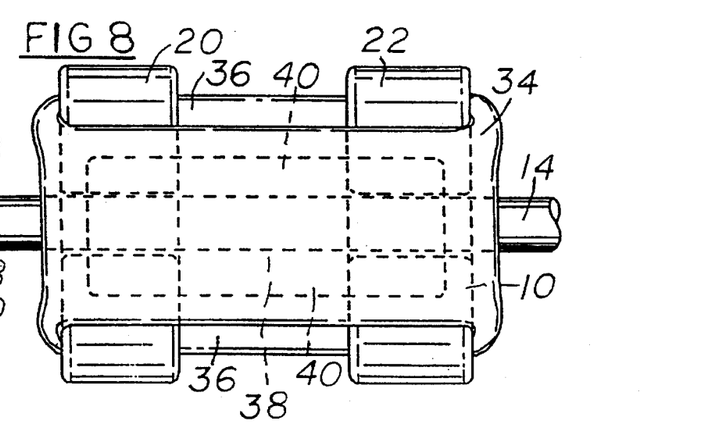
FIG. 8 is an elevation similar to FIG. 3 and showing a ligature that is a further embodiment of the invention mounted on the double tie wing bracket.
Figure 9:
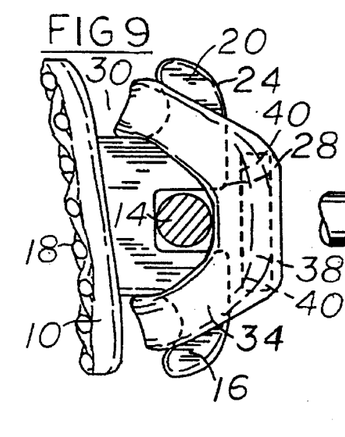
FIG. 9 is an elevation from the mesial or distal of the bracket, arch wire and ligature combination of FIG. 8.

FIGS. 8 and 9 illustrate an embodiment of the invention in which the wafer insert 40 is shorter in its mesial-distal dimension than that of the embodiment of FIGS. 3 through 6, and is also shorter than the mesial-distal dimension of the bracket body, so that the ends of the ligature body extend correspondingly beyond the mesial and distal ends of the insert and the bracket. The ligature edges can therefore wrap around the bracket ends, and have an increased possibility of protrusion into the slot, with increased possibility of frictional contact with the arch wire, especially when the arch wire is of the non-round cross-sections shown in FIGS. 10 through 13 and 15.

A substantial advantage of such stiffened or reinforced ligatures is their flexibility of application to a procedure, in that if at any stage the orthodontist decides that additional control is needed it is only necessary to replace the existing elastomeric hoop ligature with such a reinforced or stiffened ligature. Another aspect of this flexibility is that they can be designed for use in situations where minimum friction is required, or in situations where the presence of substantial friction is not important and can therefore be tolerated, or in situations where high friction is desired.

A typical situation where high binding friction is desired to inhibit sliding movement along the wire, is for example where the particular tooth is already properly positioned and there is the possibility of unwanted movement away from the optimum position under the effect of the interaction between the wire and other brackets. Thus, the engagement of the relatively rigid wire surface with the rigid lingual surface of the insert gives greater possibility of control of the movement produced by the interaction, and also gives much increased accuracy of optimum positioning of the bracket and its tooth as the wire becomes fully engaged in the slot and the mesially-distally elongated rigid member butts against both the wire and the bracket labial surface over the full mesial-distal width of the bracket.

Figure 10:
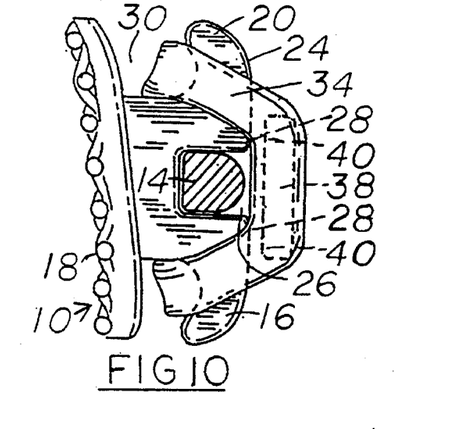
FIGS. 10 through 13 are longitudinal cross-sections similar to FIG. 6 and illustrating the use of ligatures of the invention with arch wires of different transverse cross-sections.
Figure 11:
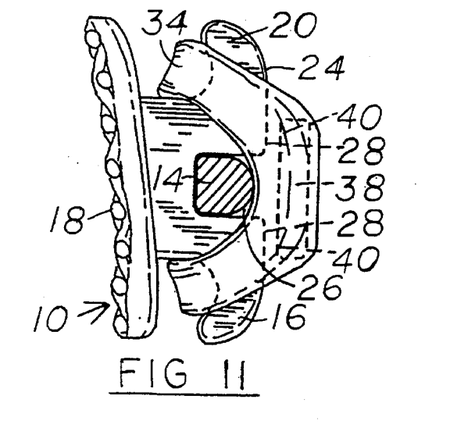

The ligatures of the invention are also suited for use with arch wires of other than round cross-section, for example those shown in FIGS. 10 through 15. The wires illustrated in FIGS. 10 through 12 and 15 have in common that their lingual-labial dimension is equal to or slightly smaller than the corresponding dimension of the slot, so that while the wire protrudes from the slot as the result of misalignment it will be relatively highly frictionally engaged by the ligature, but upon full insertion the rigid portion of the ligature will but against the bracket labial face and the friction will be reduced to a minimum value, that is however capable of adjustment by suitable design of the ligature. FIG. 10 illustrates the use of a wire of D-shape transverse cross-section in combination with a ligature of the type illustrated by FIGS. 3 through 6, while FIG. 11 illustrates the use of such a wire in combination with a ligature of the type illustrated by FIGS. 8 and 9. FIG. 10 also illustrates the use of such a wire disposed with its rounded convex face toward the labial, so that there is angled contact between the rigid flat ligature face and the wire from either the labial-gingival or the labial-occlusal direction. The use of a D-shape wire with its rounded face toward the lingual is described below.

Figure 12:
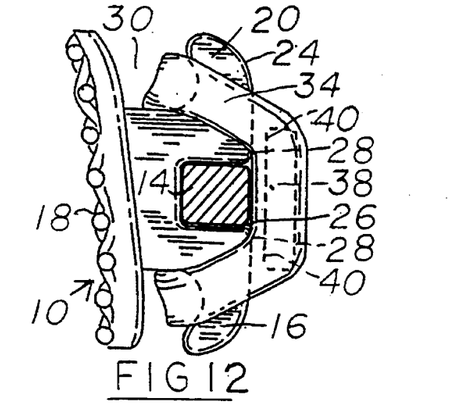
Figure 13:
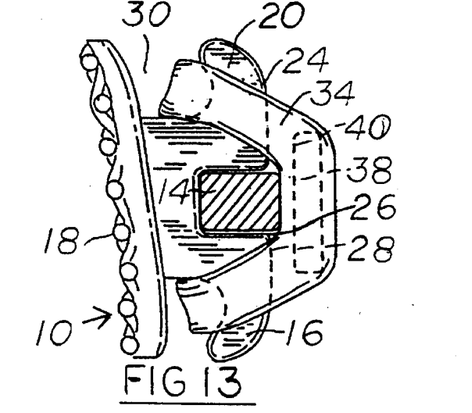

FIG. 12 illustrates the use of a ligature of the type shown in FIGS. 3 through 6 with a wire of rectangular transverse cross-section wire, while FIG. 13 illustrates the use of a ligature of the invention in combination with an arch wire of rectangular transverse cross-section and of labial-lingual dimension greater than the depth of the slot, so that even when the wire is fully engaged in the slot it still protrudes through the slot opening and is highly frictionally engaged by the ligature, the ligature of the invention providing the advantage over the prior art hoop ligatures that the engagement between the two relatively rigid surfaces provides extra control and accuracy, as described above.

Figure 14:
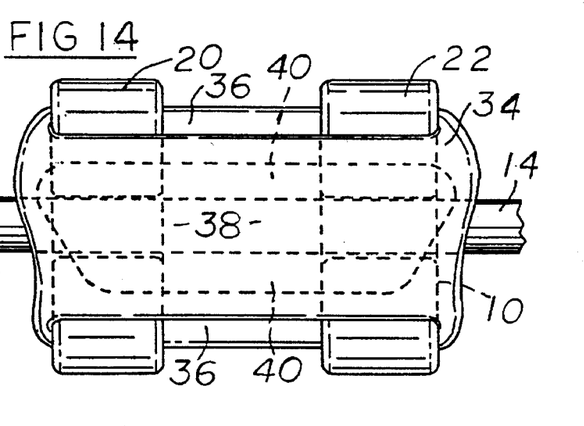
FIG. 14 (sheet 2) is an elevation similar to FIG. 3 and showing a ligature that is a further embodiment of the invention mounted on a double tie wing bracket of the type shown in FIGS. 1 and 2.
Figure 15:
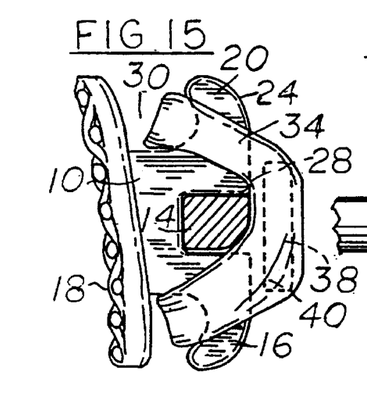
FIG. 15 (sheet 2) is an elevation from the mesial or distal of the bracket, arch wire and ligature combination of FIG. 14.

FIGS. 14 and 15 illustrate the use of an arch wire of the transverse cross-section shown in FIG. 11 of my U.S. Pat. No. 4,248,588. In such a wire the junctions between the lingual surface and the gingival and occlusal surfaces, and between the labial and occlusal surfaces, are right angled, while the junction between the labial and gingival surfaces is a smoothly curved convex surface that, with the wire protruding from the slot, when engaged by the flat rigid portion of the ligature cooperates particularly effectively therewith in producing the desired movement of the bracket by the wire because of its angled contact. A ligature intended specifically for use with such a wire can employ an insert 38 that, as shown in FIG. 14, has a mesial-distal dimension along its occlusal edge that is greater than the corresponding dimension along its gingival edge. Thus the portion of the ligature body adjacent the gingival edge has the possibility of the ligature shown in FIGS. 8 and 9 of wrapping around the bracket body edges and frictional engagement with the wire, while the occlusal portion of the insert provides the desired control engagement with the occlusal portion of the wire labial surface.

Whether or not the bracket should slide freely mesially distally along the wire depends upon the orthodontic problem and its solution, and also the technique that is used. Free sliding is required, for example, when the procedure has involved the extraction of one or more teeth (e.g. the first bicuspids) and the adjacent other teeth (the canines in this case) are to be moved into the extraction sites. The ligation force must be high to keep control of the attitudes of the teeth as they are moved, but with conventional wire and elastomeric ligatures this heavy ligation causes binding between the arch wire and the ligature that inhibits the sliding movement. With the system of the invention such hard ligation can be used while ensuring that there is adequate free sliding between the arch wire and selected brackets by using reinforced ligatures with the selected brackets and prior art ligatures at the other brackets where sliding is to be inhibited. An example of a procedure stage where sliding is to be permitted at selected brackets and prevented at others is at the end of a class II, division 1 bite relationship problem (buck teeth) where the incisors are all in good relation to one another, but the group as a whole is still in a protrusion relation to the other posterior teeth. The posterior teeth were incorrectly related but are now in a good class I (neutrocluson) relation, and there are spaces mesial to the canines that are to be filled as the incisors are retracted. The arch wire must slide freely through the posterior brackets, but there should be no sliding at all between the arch wire and the incisor brackets, so as not to lose the good relationship that has been established. The reinforced ligatures of the invention act more efficiently than the relatively soft prior art elastomeric ligatures to restrain the flat lingual insert member face parallel to the bracket labial face, while not requiring a bracket that has a separate rigid slot closure member. They also provide a better mechanical advantage if there is any tendency for the wire to rotate away from the optimum attitude, especially in applications where low sliding friction is required.

Figure 16:
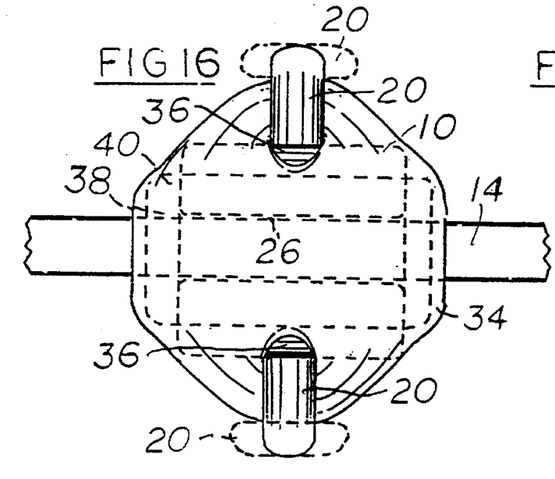
FIG. 16 is an elevation from the labial of a single tie wing bracket showing in place thereon a reinforced elastomeric ligature that is a still further embodiment of the invention.
Figure 17:
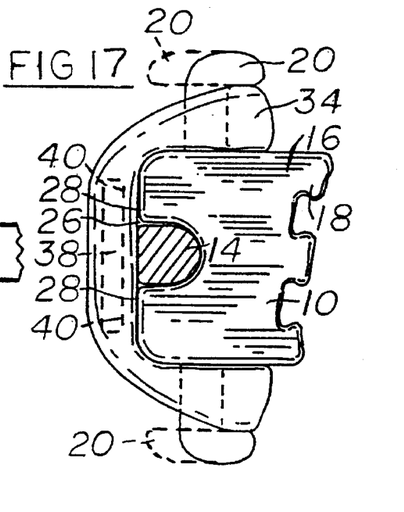
FIG. 17 is an elevation from the mesial or distal of the bracket, arch wire and ligature combination of FIG. 16.

FIGS. 16 and 17 show the application of the invention to a bracket having only a single pair of ligature retaining tie wings 20, the ligature being provided with respective round holes 36 through which the tie wings pass. The Figures also show the application of a ligature of the invention to a bracket having mushroom headed metal posts 20 which constitute ligature retaining means over which the ligature is engaged, the outline of such posts being indicated in broken lines. In general the specific dimensions and configuration of the elastomer will be tailored for the specific type of bracket with which it is to be used.

Figure 18:
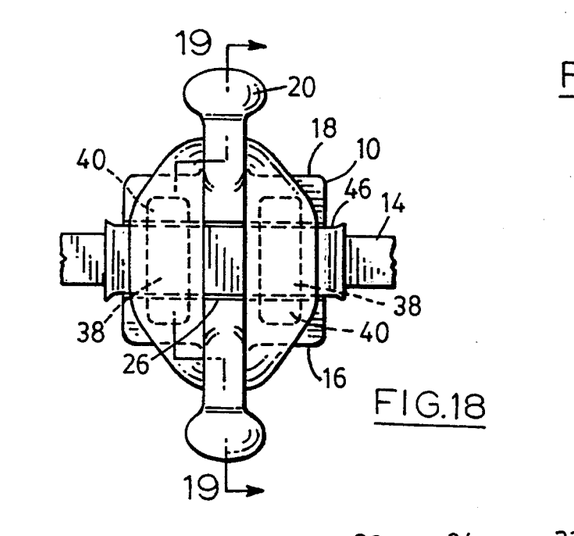
FIG. 18 is an elevation from the labial of a single tie wing bracket showing in place thereon a reinforced elastomeric hoop ligature that is a still further embodiment of the invention.
Figure 19:
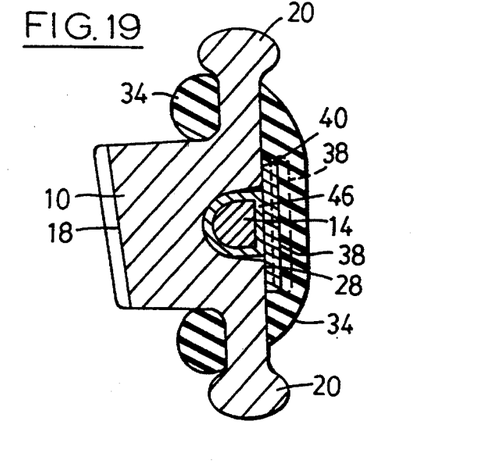
FIG. 19 is a longitudinal cross section of the bracket, arch wire and hoop ligature combination of FIG. 18, taken on the line 18—18 therein.

FIGS. 18 and 19 show the application of a reinforced hoop ligature of the invention applied to a single bracket employing a pair of gingivally-occlusally extending mushroom headed posts. As with the embodiment illustrated by FIG. 7, the body of the ligature has the form of a torus which is looped around the ligature receiving members, and it is provided with two separate diametrically opposed rigid reinforcing members 38, each of which is of gingival occlusal dimension greater than that of the slot opening.

In the application examples of FIGS. 7, 18 and 19 the wire 14 has mounted thereon a sleeve 46 which locally increases the cross-sectional dimension of the portion of the wire that is engaged in the bracket slot. The application and uses of such sleeves are more fully disclosed and are claimed in my patent application Ser. No. 08/036,639, U.S. Pat. No. 5,380, 197 from which this present application is a continuation in part.

Figure 3:
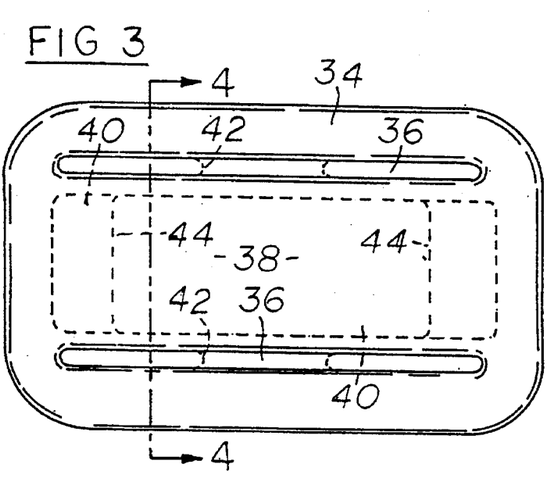
FIG. 3 is an elevation from the labial of a non-hoop reinforced elastomeric ligature that is a first embodiment of the invention, the ligature being intended for use with a double tie wing bracket of the type shown in FIGS. 1 and 2.
Figure 4:
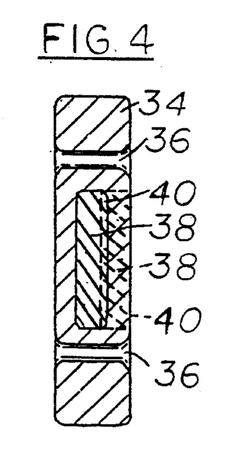
FIG. 4 is longitudinal cross-section of the ligature of FIG. 3, taken on the line 4—4 therein.
Figure 20:
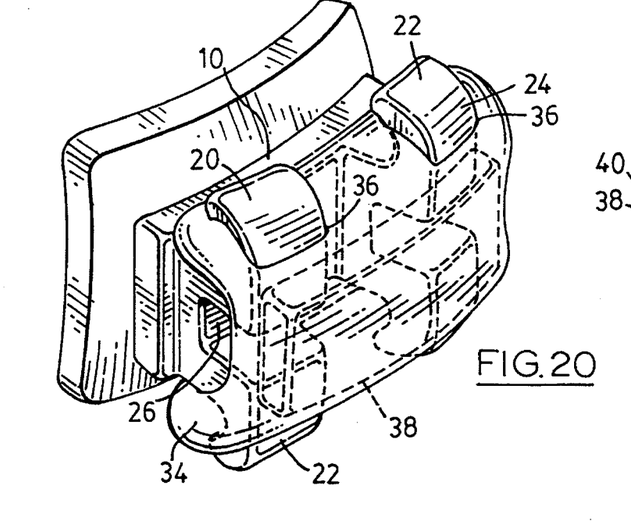
FIG. 20 is a perspective view from the labial of a double tie wing bracket having a lingual face curved in the gingival occlusal plane, and showing a reinforced ligature with a correspondingly curved rigid insert mounted thereon.

FIG. 20 shows in perspective a double tie wing bracket in which the slot lingual surface and the bracket labial surface are curved in the gingival occlusal extending plane about a radius so that the bracket conforms more closely to the curvature of the portion of the arch wire with which it is engaged. A reinforced ligature for use with such a bracket preferably has the labial and lingual faces of the reinforcing insert similarly curved, and in general it may be preferred to curve these faces to conform to at least the curvature of the bracket labial surface to maximize the operational contact between them. The ligature also has separate holes 36 through which the tie wings 20 and 22 protrude, instead of the single elongated slot of the embodiment of FIGS. 3 through 6, inhibiting the possibility of entry of foreign matter, such as food particles, between the ligature and the bracket. The possibility of the provision of separate holes instead of a single elongated slot is indicated in the embodiment of FIG. 3 by the broken lines 42. The rigid member 38 is of the same mesial-distal width as the bracket body, while the ligature body is of greater mesial-distal width than the bracket body, so that the end portions of the ligature tend under the resilience of the material to wrap around the mesial and distal ends of the bracket. This latter feature will result in frictional contact between the wire and the ligature, but the small increase involved is accepted because of the close fit of the ligature about the wire and bracket again inhibiting the possibility of entry of foreign matter, such as food particles, between the ligature, the wire and the bracket. Such a ligature can of course be used freely in situations where minimum friction is not essential.

Figure 21:
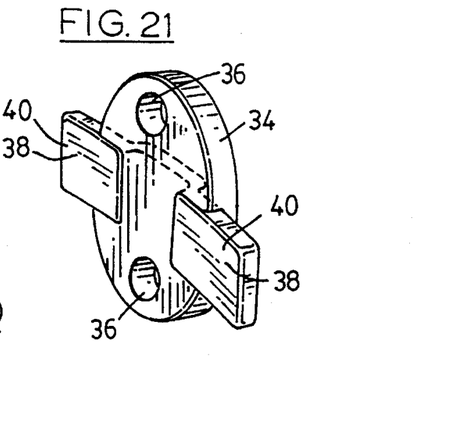
FIG. 21 is a perspective view from the lingual of a reinforced ligature with a rigid insert mounted therein that extends mesially and distally beyond the ligature body.

FIG. 21 shows an example of a ligature in which the mesial-distal dimension of the rigid insert 38 is substantially greater than the corresponding dimension of the ligature and can also be substantially greater than that of the bracket body, thereby increasing the length of the possible area of contact between the ligature and the arch wire, with correspondingly increased possibility of effective cooperation between them, especially in ensuring the desired rotational position of the bracket and the tooth. The insert is cranked at its center portion so that the center portion can be completely embedded in elastomer for its secure retention on the body, and so that the resulting two mesially-distally spaced mesial and distal end portions of the insert lingual surface not only project mesially and distally from the ligature body but are also completely free of elastomer, so that there will be metal-to-metal contact of the insert with the wire and the bracket body.

It is usually preferred for the insert to be of the maximum mesial-distal width possible because of the facilitated cooperation with the bracket and the wire, particularly rotation control about an occlusal-gingival axis, but as illustrated by FIGS. 8 and 14, and as indicated by the broken lines 44 in FIG. 3, it is also possible for the insert to be of shorter mesial distal dimension. This variation of the width of the rigid member relative to the bracket and ligature body widths, in conjunction with the variation of the placement of the member within the ligature body discussed above, permits adjustment of the amount of friction that is likely to obtained between the ligature and the wire, giving increased flexibility of application of the ligatures of the invention to a particular form of bracket and to a particular type of orthodontic procedure. For example, the minimum possible friction is obtained when the rigid member is of at least the same mesial distal width as the ligature body and has its lingual face in contact with the wire. The friction will be increased somewhat when there is a layer of elastomer between the member and the wire, and it will again be increased progressively as the elastomer layer is made thicker and as the rigid member width is shortened, with correspondingly increased possibility that elastomer can protrude into the slot or wrap around the bracket ends. There is therefore the possibility of adjustment of either one or both of these features until the ligature exhibits the desired degree of frictional engagement. An equivalent effect can be obtained by splitting the rigid member into two or more mesially distally spaced portions, the spacing being sufficient for the elastomer between the portions to protrude into the slot for the above-described frictional engagement.

By way of example, a non-hoop type elastomeric ligature intended for use with a conventional double tie wing bracket of mesial-distal width 3.9 mm (0.154 in) and with a rectangular arch wire receiving slot of gingival-occlusal height 0.56 mm (0.022 in) will have a body of about 3.9–4.5 mm (0.154–0.180 in) mesial-distal width and 2.0–2.25 mm (0.080–0.090 in) gingival-occlusal length; a stainless steel insert for such a ligature typically will have a mesial-distal width in the range 1.5–3.0 mm (0.060–0.120 in), a gingival-occlusal length in the range 0.75–1.0 mm (0.030–0.040 in), and a labial-lingual thickness in the range 0.10–0.125 mm (0.004–0.005 in). An insert of ceramic material will be of the same width and length, but its thickness will be in the range 0.20–0.25 mm (0.008–0.010 in).

Also by way of example, toroidal hoop type elastomeric ligatures as illustrated by FIGS. 7, 18 and 19 typically are of external diameter in the range 3–5 mm (0.12–0.2 in) and internal diameter in the range 2–3 mm (0.08–0.12 in); inserts for such hoops typically have a gingival-occlusal length in the range 0.76–1.02 mm (0.030–0.040 in), and a mesial-distal width in the range 0.38–0.76 mm (0.015–0.030 in); a ceramic rigid member has a labial-lingual thickness in the range 0.13–0.25 mm (0.005–0.010 in).

The brackets shown in FIGS. 16, 17, 18 and 19 are designed to be used in conjunction primarily with arch wires 14 that are of circular or of D-shape cross-section. When a D-shape cross-section wire is used it is disposed in the slot with its curved surface facing to the lingual, the slot being of D-shape cross-section but with its gingival and occlusal faces diverging away from one another gingivally and occlusally respectively at a small angle. Such brackets and arch wire combinations are described in more detail in my prior U.S. Pat. No. 5,224,858, the disclosure of which is incorporated herein by this reference. Because of the wider divergent mouth of the slot it is relatively easier to engage the wire therein at the commencement of a procedure, and the sloping engaging faces facilitate the movement of the wire into the slot under the urge provided by the wire and the ligature. As will be seen from FIGS. 17 and 19 the labial-lingual dimension of the slot corresponds to that of the wire, so that with the wire fully engaged in the slot the wire labial surface is coplanar with the bracket labial surface. The ligatures of the invention are therefore particularly effective when used in combination with such brackets and wires in that through the contact of the rigid member with the wire the ligature operates to urge the wire into the slot into the desired optimum attitude, whereupon the rigid lingual face of the ligature engages both the labial surface of the wire and the bracket labial surface border portions to maintain the wire and the bracket firmly and accurately in the desired angular relation to one another, despite the divergence of the slot gingival and occlusal surfaces.

The embodiments described are exemplary of a wide range of embodiments all of which are encompassed.

I claim:

1. An elastomeric ligature for use in combination with an orthodontic bracket and a cooperating arch wire;

the bracket comprising a bracket body having labial, lingual, gingival, occlusal, mesial and distal surfaces, and having a mesial distal extending arch wire slot with an opening at the bracket labial surface, the bracket having labial surface border portions bordering respectively the gingival and occlusal edges of the slot labial opening;

the bracket having gingivally and occlusally projecting ligature retaining members on opposite sides of the slot for the reception of a ligature, the ligature when mounted thereon having an intermediate portion which extends across the slot labial opening;

the ligature comprising a body of an elastomeric material having in the intermediate portion thereof a rigid member of a more rigid material than the elastomeric material and of gingival occlusal dimension adapted to use greater than the gingival occlusal dimension of the slot labial opening;

the rigid member having gingival and occlusal border portions and being so positioned in the ligature body that, when the ligature is mounted on the ligature retaining members, the rigid member border portions are adjacent the bracket labial surface border portions on respective sides of the labial slot opening with the rigid member extending across the labial slot opening.

2. A ligature as claimed in claim 1, wherein the mesial-distal dimension of the ligature member and of the rigid member are both adapted to be equal to the mesial-distal dimension of a bracket body with which the ligature is to be used.

3. A ligature as claimed in claim 1, wherein the mesial-distal dimension of the ligature member is adapted to be greater than the mesial-distal dimension of the bracket body with which the ligature is to be used to enable the mesial and distal ends of the ligature member to wrap around the mesial and distal ends of the bracket body.

4. A ligature as claimed in claim 1, wherein the mesial-distal dimension of the rigid member is adapted to be greater than the mesial-distal dimension of the bracket body with which the ligature is to be used.

5. A ligature as claimed in claim 1, wherein the mesial-distal dimension of the rigid member is adapted to be smaller than the mesial-distal dimension of the bracket body with which the ligature is to be used.

6. A ligature as claimed in claim 1, wherein the mesial-distal dimension of an occlusal edge of the rigid member is adapted to be greater than a mesial-distal dimension of the gingival edge thereof.

7. A ligature as claimed in claim 1, wherein the rigid member is made from a material selected from the group of materials consisting of metal and ceramic.

8. A ligature as claimed in claim 1, wherein the rigid member is of plastics material of greater rigidity than the elastomeric material.

9. A ligature as claimed in claim 1, wherein the labial and lingual surfaces of the rigid member are curved in the gingival-occlusal extending plane to correspond to the curvature of the labial surface of the bracket with which it is to be used.

10. A ligature as claimed in claim 1, wherein the lingual surfaces of the rigid member and of the ligature body are coplanar for contact of the rigid member lingual surface with the bracket labial surface.

11. A ligature as claimed in claim 1, wherein the rigid member is completely embedded within the material of the ligature body so that the rigid member lingual surface has a thin layer of the elastomeric material interposed between the rigid member lingual surface and the bracket labial surface when mounted thereon.

12. A ligature as claimed in claim 1, wherein the rigid member is completely embedded within the material of the ligature body centrally between the labial and lingual surfaces thereof.

13. A ligature as claimed in claim 1, wherein the rigid member has a central portion embedded within the ligature body and has its mesial and distal end portions projecting from the ligature body for direct contact thereof with the bracket labial surface when the ligature is mounted thereon.

14. A ligature as claimed in claim 1, and for use with a bracket comprising ligature receiving means consisting of a single pair of gingivally and occlusally extending tie wings or posts, and wherein the ligature body has therein on opposite sides of the rigid member respective apertures through which the tie wings or posts are adapted to pass with the ligature fitting tightly around the tie wings or posts.

15. A ligature as claimed in claim 1, and for use with a bracket comprising ligature receiving means consisting of two mesially-distally spaced pairs of gingivally and occlusally extending tie wings or posts, and wherein the ligature body has therein on opposite sides of the rigid member separate mesially distally spaced respective apertures through which the tie wings or posts are adapted to pass with the ligature fitting tightly around the tie wings or posts.

16. An elastomeric hoop ligature for use in combination with an orthodontic bracket and a cooperating arch wire;

the bracket comprising a bracket body having labial, lingual, gingival, occlusal, mesial and distal surfaces, and having a mesial distal extending arch wire slot with an opening at the bracket labial surface, the bracket having labial surface border portions bordering respectively the gingival and occlusal edges of the slot labial opening;

the bracket having gingivally and occlusally projecting ligature retaining members on opposite sides of the slot for the reception of a ligature;

the ligature comprising a hoop-shaped body of an elastomeric material which when mounted on the bracket body has two diametrically opposed intermediate portions each of which extends across the slot labial opening, the ligature having in each of the intermediate portions a rigid member of a more rigid material than the elastomeric material and of gingival occlusal dimension greater than the gingival occlusal dimension of the slot labial opening;

each rigid member having gingival and occlusal border portions and being so positioned in the ligature body that, when the ligature is mounted on the ligature retaining members, the rigid member border portions are adjacent the bracket labial surface border portions on respective sides of the labial slot opening with the rigid member extending across the labial slot opening.

17. A ligature as claimed in claim 16, wherein the rigid members are made from a material selected from the group of materials consisting of metal and ceramic.

18. A ligature as claimed in claim 16, wherein the rigid members are of plastics material of greater rigidity than the elastomeric material.

19. A ligature as claimed in claim 16, wherein the labial and lingual surfaces of the rigid members are curved in the gingival-occlusal extending plane to correspond to the curvature of the labial surface of the bracket with which it is used.

20. A ligature as claimed in claim 16, wherein the lingual surfaces of the rigid members and of the ligature body are coplanar for contact of the rigid member lingual surfaces with the bracket labial surface.

* * * * *